(12) United States Patent
Hower et al.

(10) Patent No.: US 6,764,652 B2
(45) Date of Patent: Jul. 20, 2004

(54) MICROMACHINED DEVICE FOR RECEIVING AND RETAINING AT LEAST ONE LIQUID DROPLET, METHOD OF MAKING THE DEVICE AND METHOD OF USING THE DEVICE

(75) Inventors: Robert W. Hower, Ann Arbor, MI (US); Richard B. Brown, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 309 days.

(21) Appl. No.: 09/768,950

(22) Filed: Jan. 24, 2001

(65) Prior Publication Data

US 2004/0071598 A1 Apr. 15, 2004

(51) Int. Cl.$^7$ .................................................. B01L 3/00
(52) U.S. Cl. ........................................ 422/99; 422/102
(58) Field of Search ................................ 436/174, 178; 204/403.4, 403.05, 403.13, 415, 418, 416; 422/52, 57, 58, 102, 99

(56) References Cited

U.S. PATENT DOCUMENTS

| | | | |
|---|---|---|---|
| 4,975,175 A | * 12/1990 | Karube et al. | ......... 204/403.12 |
| 5,200,051 A | 4/1993 | Cozzette et al. | |
| 5,334,837 A | 8/1994 | Ikeda et al. | |
| 5,376,255 A | * 12/1994 | Gumbrecht et al. | ......... 204/426 |
| 5,403,462 A | * 4/1995 | Lev et al. | ............... 204/403.15 |
| 5,955,352 A | * 9/1999 | Inoue et al. | ............. 435/287.7 |
| 6,251,567 B1 | * 6/2001 | Reinecke et al. | ........... 430/325 |
| 6,440,296 B1 | * 8/2002 | Stanzel et al. | ........... 205/777.5 |

FOREIGN PATENT DOCUMENTS

| | | |
|---|---|---|
| DE | 197 05 910 C1 | 6/1998 |
| EP | 1 053 784 A2 | 11/2000 |
| WO | 9813675 A1 * | 4/1998 |
| WO | 99/39829 | 8/1999 |
| WO | WO 00/67293 | 11/2000 |
| WO | WO 01/07161 | 2/2001 |
| WO | WO 01/83674 | 11/2001 |
| WO | WO 02/41996 | 5/2002 |

OTHER PUBLICATIONS

Hower, R.W., et al., New Solvent System For the Improved Electrochemical Performance of Screen–Printed Polyurethane Membrane–Based Solid–State Sensors, Proceedings For Transducers 95/Eurosensors IX, Jun. 1995, pp. 858–862.

Anna S., et al., An IC–Technology Compatible Automatic Method (SCZ Method) For Immobilization Membranes, vol. B1, pp. 514–517, 1990.

(List continued on next page.)

*Primary Examiner*—Alex Noguerola
(74) *Attorney, Agent, or Firm*—Brooks Kushman P.C.

(57) ABSTRACT

A micromachined device such as a solid-state liquid chemical sensor for receiving and retaining a plurality of separate liquid droplets at desired sites, a method of making the device and a method of using the device are provided. The technique works for both aqueous and solvent-based solutions. The device includes a substrate having an upper surface, and a first set of three-dimensional, thin film well rings patterned at the upper surface of the substrate. Each of the wells is capable of receiving and retaining a known quantity of liquid at one of the desired sites through surface tension. A method for patterning a membrane/solvent solution results in reproducibly-sized, uniformly-thick membranes. The patterning precision of this method allows one to place the membranes closer together, making the sensors smaller and less expensive, and the uniform film thickness imparts reproducibility to the sensors.

6 Claims, 2 Drawing Sheets

OTHER PUBLICATIONS

Bousse, L.J., et al., Silicon Micromachining in the Fabrication of Biosensors Using Living Cells, Technical Digest, IEEE Solid–State Sensor and Actuator Workshop, Hilton Head, S.C., pp. 173–176, Jun. 1990.

Eugster, R., et al., Selectivity–Modifying Influence of Anionic Sites in Neutral–Carrier–Based Membrane Electrodes, Analytical Chemistry, vol. 63, pp. 2285–2289, 1991.

Hower, R. W., et al., Study of Screen–Printed Wells in Solid–State Ion Selective Electrodes, Technical Digest, IEEE Solid–State Sensor and Actuator Workshop, Hilton Head Island, S.C., 1996.

Hjelt, Kari T., et al., Measuring Liquid Evaporation From Micromachined Wells, Sensors and Actuators 85, 2000, pp. 384–389.

Ramsey, J. Michael, et al., Microfabricated Chemical Measurement Systems, Nature Medicine, vol. 1, No. 10, Oct. 1995, pp. 1093–1096.

* cited by examiner

MICROMACHINED DEVICE FOR RECEIVING AND RETAINING AT LEAST ONE LIQUID DROPLET, METHOD OF MAKING THE DEVICE AND METHOD OF USING THE DEVICE

TECHNICAL FIELD

This invention relates to micromachined devices for receiving and retaining at least one liquid droplet, methods of making the devices and methods of using the devices.

BACKGROUND ART

In many applications, from the fabrication of solid-state chemical sensors to preparation of biomedical test plates, it is important to be able to dispense a known quantity of liquid onto a solid surface, and to have it confined to desired lateral dimensions, A good example of this is the deposition of polymeric membrane solutions for potentiometric liquid chemical sensors. The size (and therefore cost) of these sensors is usually determined by the membrane dimensions and spacing.

The size of integrated ion sensors is dictated by the size and spacing of their polymeric membranes, rather than by the size of the associated circuitry. Polymeric membranes have been developed for automated deposition by screen printing, as shown by R. W. Hower et al., "New Solvent System for the Improved Electrochemical Performance of Screen-Printed Polyurethane Membrane-Based Solid-State Sensors", PROCEEDINGS FOR TRANSDUCERS 95/EUROSENSORS IX, June 1995, pp. 858–862.

Such automated deposition can also be done with dispensing equipment as shown by S. Anna et al., "An IC-Technology Compatible Automatic Method (SCZ Method) for Immobilization Membranes", SENSORS AND ACTUATORS, vol. B1, pp. 514–517, 1990.

In both cases, membrane components are dissolved in solvents which are evaporated subsequent to deposition. The area occupied by an array of these membranes can be significantly reduced through the use of wells, areas separated by barrier walls, into which the membrane solutions are deposited. Thick wells for screen-printed membranes are shown by the above-noted article by Hower et al.

Membrane design rules are typically dictated by the requirement of keeping membranes which are selective to different chemicals from touching. If these membranes touch, their ionophores intermix, causing cross-contamination. As mentioned above, membranes can be deposited automatically by either screen-printing or dispensing equipment. The membrane components are dissolved in solvents to form a paste for screen-printing or a liquid for dispensing. Membrane design rules have needed to allow for flow-out of the paste or dispensing solution after it is applied to the sensor surface, making the sensors much larger than they would otherwise need to be.

To reduce the size of screen-printed sensor arrays, wells, as illustrated in FIGS. 1a and 1b, have been formed which limit the flow-out of the membrane components, allowing membranes to be smaller and closer together, as further shown in the above-noted article by Hower et al. These wells provide the additional advantage of making final membrane thickness more uniform and the deposition process more tolerant of variations in the viscosity of membrane solutions.

Epoxies, acrylic photo polymers, thick film polyimide, and silicon have been used to form wells or cavities, as further shown in U.S. Pat. No. 5,200,051 issued to Cozzette et al., and the articles by L. J. Bousse et al., "Silicon Micromachining in the Fabrication of Biosensors Using Living Cells", TECHNICAL DIGEST, IEEE Solid-State Sensor and Actuator Workshop, Hilton Head, S. C., p. 173–6; June 1990; and R. Eugster et al., "Selectivity-Modifing Influence of Anionic Sites in Neutral-Carrier-Based Membrane Electrodes", ANALYTICAL CHEMISTRY, vol. 63, pp. 2285–2289 (1991).

The approaches previously described are quite acceptable for screen-printed silicone and polyurethane membranes, as they are viscous, thixotropic pastes.

Several epoxies have excellent chemical compatibility with the membranes as well as good membrane adhesion and screen-printing properties, as shown by the article by R. W. Hower et al., "Study of Screen-Printed Epoxies for Wells in Solid-State Ion Selective Electrodes", TECHNICAL DIGEST, IEEE Solid-State Sensor and Actuor Workshop, Hilton Head Island, S.C., 1996. Membrane solutions optimized for dispensing, on the other hand, have low viscosities and a high solvent-to-solids ratio to keep the dispensing tip from clogging; the composition of a typical membrane is over 90% solvent. When these low-viscosity membrane cocktails are dispensed into the thick wells, the membranes wick out of the wells through surface tension, thinning the resulting membranes and enlarging the required membrane area.

Microsensors are sensors that are manufactured using integrated circuit fabrication technologies and/or micromachining. Integrated circuits are fabricated using a series of process steps which are done in batch fashion, meaning that thousands of circuits are processed together at the same time in the same way. The patterns which define the components of the circuit are photolithographically transferred from a template to a semiconducting substrate using a photosensitive organic coating. The coating pattern is then transferred into the substrate or into a solid-state thin-film coating through an etching or deposition process. Each template, called a "mask", can contain thousands of identical sets of patterns, with each set representing a circuit. This "batch" method of manufacturing is what makes integrated circuits so reproducible and inexpensive. In addition, photoreduction enables one to make extremely small features. The resulting integrated circuit is contained in only the top ¼ micron or so of the semiconductor substrate and the submicron thin films on its surface. Hence, integrated circuit technology is said to consist of a set of planar, microfabrication processes.

Micromachining refers to the set of processes which produce three-dimensional microstructures using the same photolithographic techniques and batch processing as for integrated circuits. Here, the third dimension refers to the height above the substrate of the deposited layer or the depth into the substrate of an etched structure. Micromachining produces third dimension in the range of 1–500 $\mu$m (typically). The use of microfabrication to manufacture sensors produces the same benefits as it does for circuits: low cost per sensor, small size, and highly reproducible behavior. It also enables the integration of signal conditioning, compensation circuits and actuators, i.e., entire sensing and control systems, which can dramatically improve sensor performance for very little increase in cost. For these reasons, there is a great deal of research and development activity in microsensors.

DISCLOSURE OF INVENTION

An object of the present invention is to provide a micromachined device for receiving and retaining at least one liquid droplet, method of making the device and method of using the device wherein the at least one droplet is retained on the device through surface tension.

In carrying out the above object and other objects of the present invention, a micromachined device for receiving and retaining a liquid droplet at a desired site is provided. The device includes a substrate having an upper surface, and a three-dimensional, thin film well patterned at the upper surface of the substrate. The well is capable of receiving and retaining a known quantity of liquid at the desired site through surface tension.

In further carrying out the above object and other objects of the present invention, a micromachined device for receiving and retaining at least one liquid droplet at a desired site is provided. The device includes a substrate having an upper surface, and a first three-dimensional, thin film well patterned at the upper surface of the substrate. The first well is capable of receiving and retaining a first known quantity of liquid at the desired site through surface tension. The devices also includes a second three-dimensional, thin film well patterned at the upper surface of the substrate. The second well is patterned outside and concentric to the first well and is capable of receiving and retaining a second known quantity of liquid at the desired site through surface tension.

In further carrying out the above object and other objects of the present invention, a micromachined device for receiving and retaining a plurality of separate liquid droplets at desired sites is provided. The device includes a substrate having an upper surface, and an array of three-dimensional, thin film wells patterned at the upper surface of the substrate. Each of the wells is capable of receiving and retaining a known quantity of liquid at one of the desired sites through surface tension.

In further carrying out the above object and other objects of the present invention, a micromachined device for receiving and retaining a plurality of separate liquid droplets at desired sites is provided. The device includes a substrate having an upper surface, and a first array of three-dimensional, thin film wells patterned at the upper surface of the substrate. Each of the wells is capable of receiving and retaining a known quantity of liquid at one of the desired sites through surface tension. The device also includes a second array of three-dimensional, thin film wells patterned at the upper surface of the substrate. Each well of the second array of wells is patterned outside and concentric to one well of the first array of wells to receive and retain a second known quantity of liquid at the desired site through surface tension.

Each of the wells may be a ring.

The device may be a microsensor wherein each of the desired sites is a sensing site. The microsensor may be a solid-state, liquid chemical sensor.

The microsensor may be a gas sensor or an optical sensor.

The device may be a biomedical test plate.

Each of the wells may be made of a photo-patternable material wherein the material may be a negative photo-patternable material.

The negative photo-patternable material may be a polymer wherein the polymer may be a polyimide.

The negative photo-patternable material may also be an epoxy wherein the epoxy may be SU8.

The substrate may be a semiconductor substrate and may include a silicon wafer.

The semiconductor substrate may further include a layer of insulating material on which the wells are patterned.

The substrate may be made of a material other than a semiconductor material.

The device may be a potentiometric liquid chemical sensor wherein each desired site is a sensing site.

The device may also be an integrated ion sensor wherein each desired site is a sensing site.

Each of the wells may include a side wall having an outside corner with a small radius to prevent its liquid droplet from flowing down outside the side wall.

In further carrying out the above object and other objects of the present invention, a method of making a micromachined device which is capable of receiving and retaining at least one liquid droplet is provided. The method includes providing a substrate having a layer of radiation-sensitive material formed thereon. The method also includes patterning at least one three-dimensional, thin film well from the layer of material. The at least one well is capable of receiving and retaining a known quantity of liquid through surface tension.

The method may further include patterning a three-dimensional, thin film well from the layer of material outside and concentric to the at least one well at the same time as patterning the at least one well.

The layer of material may be photo-patternable.

A method of using a device which has one well is further provided. The method includes dispensing a membrane solution droplet into the well wherein the membrane solution may be a polymeric membrane solution, an aqueous solution, or a solvent-based solution.

The membrane may be an optical membrane.

A method of using a device which as a second well outside and concentric with a first well includes dispensing a first membrane solution droplet into the first well, and dispensing a second membrane solution droplet over the first membrane solution droplet and into the second well.

The first membrane solution may be an internal filling solution.

The second membrane solution may be an external binding layer.

The second membrane solution may have enzymes, antibodies or fictional groups trapped therein.

A method of using a device which has a first array of wells is further provided. The method includes dispensing a membrane solution droplet into each of the wells of the array.

A method of using a device which has first and second arrays of wells wherein each of the second array of wells is outside and concentric with a well of the first array includes dispensing a first membrane solution droplet into each of the first array of wells, and dispensing a second membrane solution droplet over each of the first membrane solution droplets and into each of the second array of wells.

The substrate may be a semiconductor substrate such as a silicon wafer. The semiconductor substrate may further include a layer of insulating material on which the wells are patterned. The insulating material may include silicon nitride, silicon dioxide, silicon carbide, diamond, Teflon, etc.

The substrate may be made of glass, ceramic, plastic, metal, or other material.

Each of the wells preferably has a side wall with a rounded outside corner. An outside edge of each of the wells may have a negative profile or, alternatively, have other profiles such as vertical or positive profiles. In all cases, it is preferable to have a small radius at the outside corner.

The technique works for both aqueous and solvent-based solutions.

These wells can be utilized for containing any solution either aqueous or a solvent-based polymer film in a reproducible fashion, with reduced size and decreased spacing.

Polymer wells of the invention can be used to contain a polymer film used as a preconcentrator for a micromachined gas chromatograph system. These membranes can be cast in much the same way as the liquid chemical sensors, providing a small reproducible surface area and volume membranes to be used in this device.

The invention can also be used to pattern membranes for optically coupled sensors, in which the opacity of the membrane changes with chemical concentration.

The wells can be used to contain multilevel membranes, such as those using an internal filling solution, and an external binding layer.

A second set or array of well rings, photo-patterned at the same time as the first set or array, can be used to isolate functional groups on top of ion-selective membranes. The improved functionality can be accomplished by entrapping enzymes, antibodies, or functional groups, which can be later used to photo immobilize enzymes or antibodies, on the surface. A second membrane is dispensed on top of the first membrane with the functional groups entrapped in this external membrane. The external membrane will completely cover the first, and will flow out to the outer rings. This asymmetric membrane allows the liquid chemical sensors to monitor chemicals other than ions and in much lower concentrations, by catalyzing a reaction and detecting a byproduct. Using this asymmetric membrane technique, it is often very important to reproducibly immobilize known quantities of enzyme or antibody on the surface to get a reproducible signal. Often these devices are one-shot sensors and cannot be calibrated. Using these wells allows the mass production of reproducible enzyme or antibody layers on the surface of the ISE (ion selective electrode).

The device, method for making the device, and the method for using the device of the present invention are general. While particular implementations of the invention are disclosed herein, it would work with other materials having similar surface properties as well. There are many potential uses for this invention even though the invention was specifically developed for solid-state liquid chemical sensors.

The above object and other objects, features, and advantages of the present invention are readily apparent from the following detailed description of the best mode for carrying out the invention when taken in connection with the accompanying drawings.

BRIEF DESCRIPTION OF DRAWINGS

FIG. 1b is a side view, partially broken away and in cross-section, of one of the wells of FIG. 1a;

BEST MODE FOR CARRYING OUT THE INVENTION

In general, the device and method of the present invention utilizes thin-film materials, typically deposited by spin-coating and patterned with photolithography in a particular way to form wells which can contain a dispensed membrane/solvent droplet through surface tension. Two materials are specifically identified for use as well materials: the polymer, polyimide, and the epoxy, SU8. Many other materials would also work.

Figure 1A:
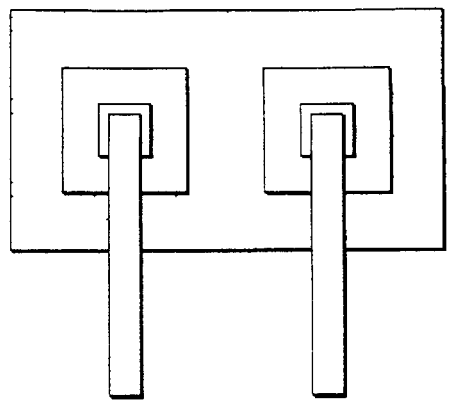
FIG. 1a is a top plan view of thick film wells surrounding an ion selective electrode sensing site for screen-printed membranes.
Figure 1B:
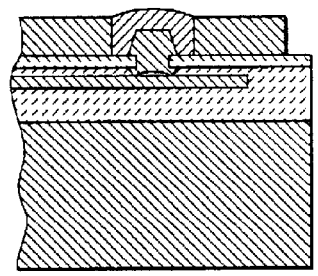
Figure 2A:
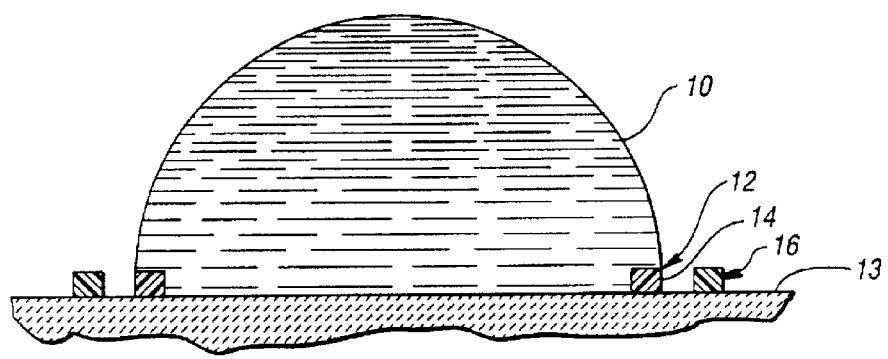
FIG. 2a is a schematic side view, partially broken away and in cross-section, of a membrane/solvent solution dispensed into a thin-film well of the present invention just after deposition.
Figure 2B:
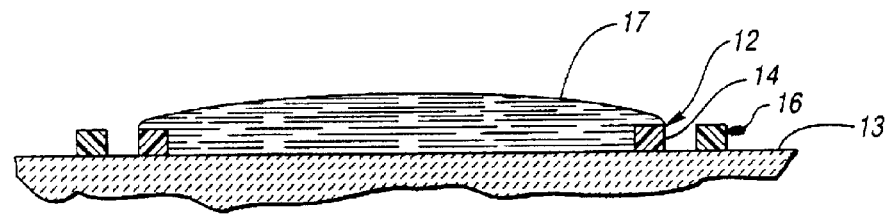
FIG. 2b is a view similar to FIG. 2a, but after evaporation of the solvent.
Figure 4:
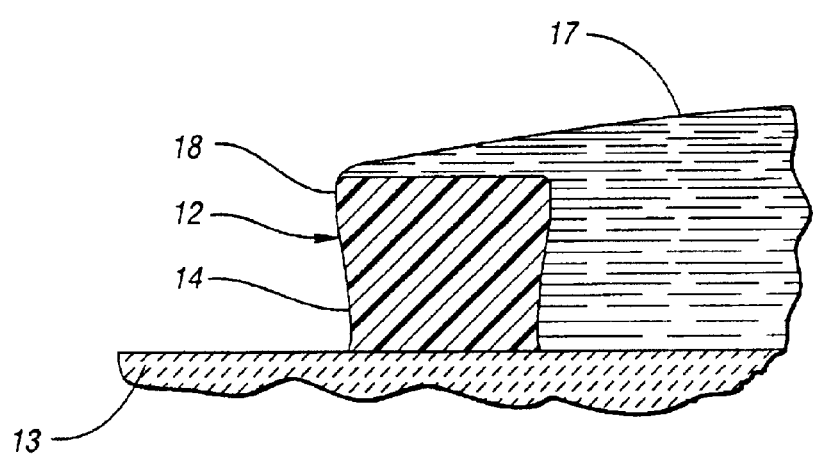
FIG. 4 is a side view, partially broken away and in cross-section, of an SU8 well ring having a negative outside edge profile and rounded outside corner which thereby contains the dispensed membrane within the well.

FIGS. 2a and 2b show the thin well approach for dispensed membranes of the present invention. To achieve membranes of the desired thickness, it is necessary to confine a large amount of membrane/solvent solution in a small area. When a membrane 10 is deposited, it covers the top of an inner well, generally indicated at 12, formed on an insulating layer 13 of a semiconductor substrate. Surface tension in the membrane solution 10 stops it from flowing past a vertical wall 14 at a rounded outside edge or corner 18 of the well 12, as best shown in FIG. 4.

A second ring 16 may be patterned outside of the first in case the membrane flows past the first ring 12. These wells can contain large droplets of membrane solution. For example, a 640 $\mu$m diameter ring can hold approximately 0.05 to 0.10 $\mu$l of membrane solution; since the membrane solution is initially mostly solvent, it is much thinner when dried, as shown at 17 in FIG. 2b.

Figure 3:
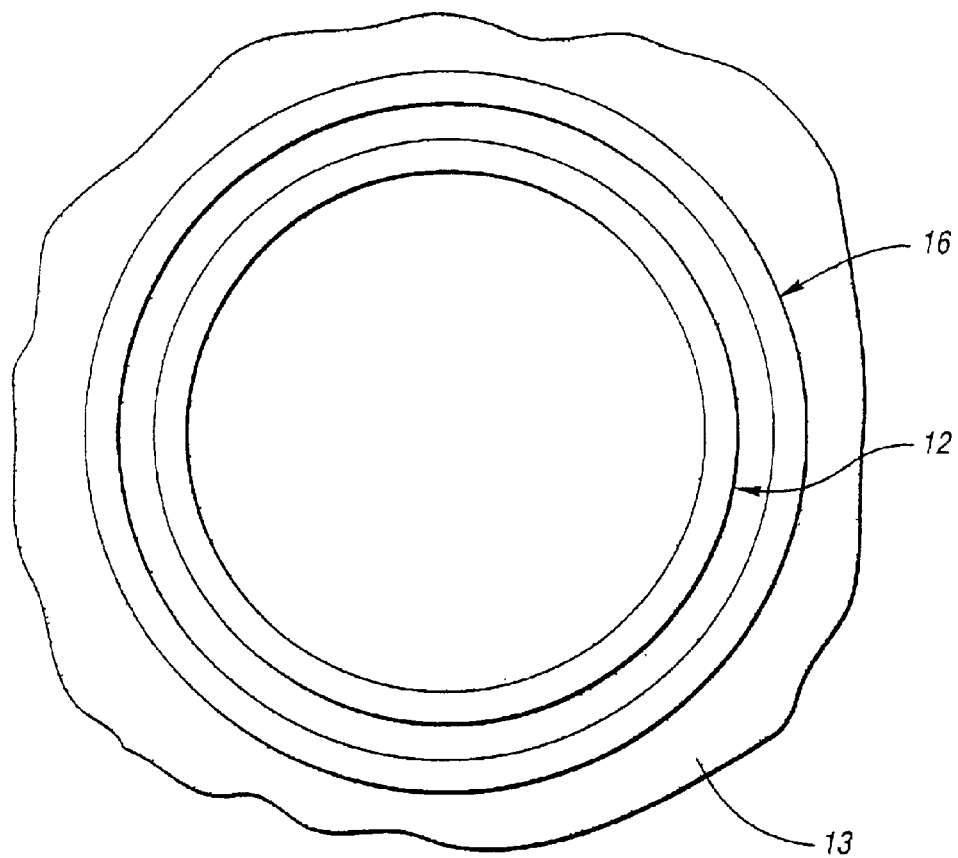
FIG. 3 is a top plan view of concentric thin-film wells of the present invention.

As seen in FIG. 3, a second set of rings, patterned at the same time as the first, allows an outer membrane to be dispensed over a first/internal membrane, enabling one to conveniently use a saturated internal membrane to improve electrochemical stability. Here, a 300 $\mu$m diameter ring was used for the internal membrane, with a 750 $\mu$m external membrane, which contained up to 0.2 $\mu$l of membrane/solvent solution. The wells give the membranes a uniform size, shape and thickness, and make the final dimensions largely independent of the viscosity of the membrane cocktail.

A key to the thin film wells containing the membrane is the profile of the outer edge or corner 18 of the thin film well material. The well 12 has a rounded outside edge profile. The rounded outside edge profile has a small radius. The negative slope of the side walls, as seen in FIG. 4, helps to contain the membrane from flowing down the outside of the well, allowing surface tension to contain the membrane.

Sensor Fabrication

While others have used polyimide to encapsulate a sensor, as mentioned in the above-noted patent, the present invention uses it to form wells for confining the membranes in the desired regions. DuPont's Pyraline PD and SU8 may be used to form the thin wells. Pyraline is easily deposited in thicknesses of 2 to 10 $\mu$m and SU8 is typically deposited in 20 to 50 $\mu$m thick layers. They both have excellent adhesion to the silicon nitride surface of the sensors, and neither significantly contaminates the ion-selective membranes. Both are photo-patternable, so the wells can be formed by spinning the material onto wafers and defining the rings in one easy photostep. Pyraline is fully imidized at 400° C., and SU8 is fully cured at 150° C., temperatures that are compatible with the special metallization used for the ISEs.

Dispensing System

When dispensing the small amount of membrane necessary for the microchemical sensors of the present invention, it is necessary to make the droplet accurate and reproducible. This is especially important for optical membranes for which the senor response is proportional to the thickness of the membrane.

The thin film wells of the present invention can contain dispensed membrane and solvent, which have a much greater height than the thickness of the well, through surface tension. It is important to get the correct and reproducible sized droplet while dispensing ISE or optical membranes. While it is less important for exact thicknesses of ISE membranes, which function independently of membrane thickness, optical membrane response is directly proportional to the thickness. When screen-printing membranes, the droplet size is determined by the size of the opening in the stencil mask. However, when using thin film wells of the present invention and dispensed membranes, it is important to produce accurate, very small, reproducible droplets. To achieve this, commercially available dispensing systems may be used.

Several important points were discovered in selecting a suitable dispensing system. First, use a positive displacement system. Most extremely small volume dispensing systems are designed for the dispensing of water-soluble solutions. Even though the membrane cocktails are mostly solvent, these solutions have a higher viscosity than the solutions normally dispensed by such equipment. The higher than normal viscosity of the membrane solution makes it necessary to push the cocktail out a dispensing tip that is quite small, in order to dispense onto small sites, requiring high pressures. Second, do not allow air bubbles into the system. Any air bubbles in the syringe will compress during dispensing, causing the membrane to ooze slowly out of the tip as the gas expands, giving non-uniform volume from site-to-site. Third, fill the syringe slowly to avoid exceeding the low vapor pressure associated with the solvents used in the membranes, which can cause gas bubbles. Fourth, use a stopcock to fill both the syringe and the tubing to eliminate the gas bubbles.

The small droplets needed for the ISE or optical membranes may be generated using a Hamilton syringe pump with a 50 $\mu$L syringe set to move 1/1000th of its travel range, effectively delivering a reproducible 50 $\mu$L droplet. This volume is very reproducible from site-to-site. One can calculate the final membrane thickness from a droplet volume using a cylindrical approximation of the final membrane and subtracting the volume of the polyimide well ring. Assuming that all of the membrane solvent evaporates, the final volume of the membrane is equal to (the amount dispensed)×(percentage solids). Combining these yields the equation:

$$T = \frac{\frac{4VK_{ps}}{\pi} + t(d_o^2 + d_i^2)}{d_o^2} \quad (1)$$

where:
T is the final thickness of the membrane;
t is the thickness of the polymer well ring;
$K_{ps}$ is the fraction solids vs. membrane volume in the dispensed membrane;

V is the volume of he membrane cocktail dispensed;
$d_o$ is the outer diameter of the ring; and
$d_i$ is the inner diameter of the ring.

By changing the solvent-to-membrane ratio, the thickness of the membrane can be easily adjusted. It was discovered that dispensing a consistent volume droplet guaranteed that the membrane would not flow past the first well. With smaller than optimal droplet size, the membrane would not completely fill the well, yielding non-uniform membrane with an unknown thickness. For optical sensors, uniform thin membranes are required.

Excellent manufacturing yield and uniformity have been obtained with the thin well approach of the present invention, which reduces the cost of sensor arrays by allowing much closer spacing of the sensors. Sensor sites can have less than 200 $\mu$m between the edges of the membranes. The adhesion of the membranes to the polyamide or SU8 surface is equivalent to the adhesion to silicon nitride.

Thin film wells of the present invention have been shown to allow smaller, and more reproducible membranes to be placed on sensing sites. These improvements have significantly improved the yield of these sensors, and enabled the fabrication of arrays of optical sensors.

When sputtered chioridized silver metal is used as the solid contact, thin dispensed membranes with thin film wells have been found to significantly improve sensor reproducibility. The membrane cocktail is held in place by surface tension until it is cured to produce a uniform thickness membrane.

A well-controlled dispensing system is necessary to get membranes the same size and thickness from site-to-site. This is especially important for optical membranes where the signal is dependent on the membrane thickness. Utilizing the wells with a commercially available dispensing system allows less initial calibration to be done on the sensors as they will behave similarly due to uniformity of sizes, thicknesses, and shapes.

While the best mode for carrying out the invention has been described in detail, those familiar with the art to which this invention relates will recognize various alternative designs and embodiments for practicing the invention as defined by the following claims.

What is claimed is:

1. A micromachined device comprising:

a substrate having an upper surface; and an array of three-dimensional, thin film wells patterned at the upper surface of the substrate wherein each of the wells is capable of receiving and retaining a know quantity of liquid;

wherein each of the wells includes a side wall having an outside corner with a small radius to prevent the liquid from flowing down outside the side wall.

2. A method of making a micromachined device comprising;

providing a substrate having a layer of radiation-sensitive material formed thereon;

patterning at least one three-dimensional, thin film well from the layer of material wherein the at least one well is capable of receiving and retaining a known quantity of liquid; and dispensing a first membrane solution into the well wherein the membrane is an optical membrane.

3. A method of making a micromachined device comprising:
   providing a substrate having a layer of radiation-sensitive material formed thereon;
   patterning at least one three-dimensional, thin film well from the layer of material wherein the at least one well is capable of receiving and retaining a known quantity of liquid;
   dispensing a first membrane solution into the well;
   patterning a three-dimensional, thin film well from the layer of material outside of at least one well at the same time as patterning the at least one well,
   dispensing a second membrane solution over the first membrane solution and into the thin film well outside the at least one well.

4. The method as claimed in claim 3 wherein the first membrane solution is an internal filling solution.

5. The method as claimed in claim 3 wherein the second membrane solution is an external binding layer.

6. The method as claimed in claim 3 wherein the second membrane solution has ionophores, enzymes, antibodies or functional groups trapped therein.

* * * * *